United States Patent
Brouillette et al.

(10) Patent No.: US 9,255,665 B2
(45) Date of Patent: Feb. 9, 2016

(54) MECHANISM FOR PUNCTURING A GAS CARTRIDGE

(71) Applicant: SOCPRA SCIENCES ET GÉNIE, S.E.C., Sherbrooke (CA)

(72) Inventors: Martin Brouillette, Sherbrooke (CA); Steven Dion, Sherbrooke (CA); Christian Hebert, Shawinigan (CA)

(73) Assignee: SOCPRA SCIENCES ET GENIE S.E.C., Sherbrooke, Quebec (CA)

( * ) Notice: Subject to any disclaimer, the term of this patent is extended or adjusted under 35 U.S.C. 154(b) by 0 days.

(21) Appl. No.: 14/363,474

(22) PCT Filed: Dec. 13, 2012

(86) PCT No.: PCT/CA2012/001142
§ 371 (c)(1),
(2) Date: Jun. 6, 2014

(87) PCT Pub. No.: WO2013/086612
PCT Pub. Date: Jun. 20, 2013

(65) Prior Publication Data
US 2014/0361036 A1    Dec. 11, 2014

Related U.S. Application Data

(60) Provisional application No. 61/570,911, filed on Dec. 15, 2011.

(51) Int. Cl.
*F17C 13/00*    (2006.01)
*A61M 5/30*    (2006.01)
(Continued)

(52) U.S. Cl.
CPC .............. *F17C 13/00* (2013.01); *A61M 5/2053* (2013.01); *A61M 5/30* (2013.01); *B63C 9/19* (2013.01);
(Continued)

(58) Field of Classification Search
CPC ................ B63C 9/19; B63C 2009/007; F17C 2205/032
USPC .......................................... 222/399, 5, 81–83
See application file for complete search history.

(56) References Cited

U.S. PATENT DOCUMENTS 1,772,674 A * 8/1930 Markus ........................... 441/94
2,513,347 A * 7/1950 Myers ................................ 222/5
(Continued)

FOREIGN PATENT DOCUMENTS

FR    2804329 A1    8/2001
FR    2800619 B1    2/2002
(Continued)

OTHER PUBLICATIONS www.bioject.com.
(Continued)

*Primary Examiner* — Donnell Long
(74) *Attorney, Agent, or Firm* — BCF LLP (57) ABSTRACT

A mechanism for puncturing gas cartridges comprises a lever comprising a short lever arm and a long lever arm, both arms extending from a pivot. The mechanism also comprises a ramp for pushing laterally a tip of the long lever arm under application of an input force on the ramp. The lever is configured to rotate about the pivot under lateral movement of the tip of the long lever arm, causing a tip of the short lever arm to apply a puncturing force between the gas cartridge and a puncturing member. A main body may receive the gas cartridge, the puncturing member and the lever. An actuator may be slidably mounted on the main body for applying the input force on the ramp by sliding towards the main body. The mechanism may be incorporated in a gas injection device or in a needleless syringe.

18 Claims, 11 Drawing Sheets

(51) Int. Cl.
  *B63C 9/19* (2006.01)
  *A61M 5/20* (2006.01)
  *F17C 7/00* (2006.01)
  *B63C 9/00* (2006.01)

(52) U.S. Cl.
  CPC ............ *F17C 7/00* (2013.01); *B63C 2009/007* (2013.01); *F17C 2205/0302* (2013.01); *F17C 2205/032* (2013.01); *F17C 2270/0772* (2013.01)

(56) References Cited

U.S. PATENT DOCUMENTS

| | | | |
|---|---|---|---|
| 2,680,439 A | | 6/1954 | Sutermeister |
| 2,946,484 A | * | 7/1960 | Stoner ............... 222/5 |
| 3,246,801 A | | 4/1966 | De Boer ............ 222/5 |
| 3,426,942 A | * | 2/1969 | Friedman et al. ........ 222/5 |
| 3,490,649 A | | 1/1970 | Sheridan |
| 3,494,506 A | | 2/1970 | Fujimoto |
| 3,834,433 A | | 9/1974 | Thompson |
| 3,883,043 A | * | 5/1975 | Lane ............... 222/82 |
| 3,905,750 A | * | 9/1975 | Sell ............... 431/142 |
| 4,446,990 A | * | 5/1984 | Stevenson et al. ....... 222/82 |
| 4,524,885 A | | 6/1985 | Zimmerly |
| 4,596,556 A | | 6/1986 | Morrow et al. |
| 5,007,368 A | | 4/1991 | Bush |
| 5,024,656 A | | 6/1991 | Gasaway et al. |
| 5,643,030 A | | 7/1997 | Brown |
| 5,887,764 A | * | 3/1999 | Ennis et al. ............. 222/389 |
| 6,047,865 A | | 4/2000 | Shervington et al. |
| 6,096,002 A | | 8/2000 | Landau |
| 6,406,455 B1 | | 6/2002 | Willis et al. |
| 6,572,581 B1 | | 6/2003 | Landau |
| 6,783,509 B1 | | 8/2004 | Landau et al. |
| 7,156,257 B2 | | 1/2007 | de la Serna |
| 2002/0084282 A1 | * | 7/2002 | Wu ............... 222/5 |
| 2002/0188251 A1 | | 12/2002 | Staylor et al. |
| 2003/0168480 A1 | * | 9/2003 | Kim ............... 222/399 |
| 2008/0038970 A1 | | 2/2008 | Isberg et al. |

FOREIGN PATENT DOCUMENTS

| | | |
|---|---|---|
| WO | 02/098479 A2 | 12/2002 |
| WO | 03/041762 A2 | 5/2003 |
| WO | 2005/118033 A2 | 12/2005 |
| WO | 2006/047087 A2 | 5/2006 |
| WO | 2006/073394 A1 | 7/2006 |

OTHER PUBLICATIONS www.mustangsurvival.com/hydrostatic-inflator/index.php.
www.crossject.com.
www.penjet.com.
http://maximuminflation.com/tires_new.html.
V86160 Manual Inflator Rearming/Status Indicator Instructions, Leland, 2005.

* cited by examiner

MECHANISM FOR PUNCTURING A GAS CARTRIDGE

TECHNICAL FIELD

The present disclosure relates to the field of gas delivery systems, yore specifically, the present disclosure relates to a mechanism for puncturing a membrane of a gas cartridge.

BACKGROUND

Compressed gas contained in a gas cartridge, for example a single-use gas cartridge, is often employed as a reliable and quick source of energy in diverse fields including emergency inflating devices, cooking tools and paintball guns. These disposable cartridges are usually sealed with a clamped membrane from which gas is released by puncturing the membrane. Some applications may require high power density which involves gas pressures that may exceed a hundred times the atmospheric pressure. Thereby, for security and handling reasons, the membrane is made strong enough to prevent any unintended gas release and is therefore hard to puncture manually without a certain level of mechanical advantage.

With each new application of these cartridges may come a new technique to force a puncturing member, for example a punch through the membrane, or to force the membrane onto the puncturing member to release the gas. As a result many solutions currently exist from which designers may pick from to ease the use of these cartridges in their respective devices. Frequently encountered mechanisms use a lever or a screw to produce the required mechanical advantage allowing a user to pierce the cartridge membrane with its lone hand strength. Other designs rely on energy stored, for example, by means of a pre-compressed spring, in which the energy is released by the user with minimal force for pushing the puncturing member against the cartridge membrane or for pushing the membrane onto the puncturing member. A frequent problem resulting from the use of a pre-compressed spring is that components that maintain the spring in a compressed position may gradually suffer from plastic deformation, reducing an amount of energy stored in the spring. For some applications, use of a pre-compressed spring may also be dangerous because of possible unintended release of the energy storing mechanism, due to a shock or to mishandling.

Earlier solutions may not be adequate depending on constraints inherent to some applications. Also, design constrains may be of several kinds including device's final size, cost, fabrication process, storage duration and conditions, final usage and so on.

Some earlier pressurized gas cartridge concepts reduce the necessary force to break the seal and release the gas. A gas cartridge proposed in U.S. Pat. No. 6,047,885, issued Apr. 11, 2000, features an elongated stem attached to a closure member of the gas cartridge that, when pushed sideways, allows to easily break the seal with a minimal lateral force. This type of gas cartridge is difficult to manufacture and is prone to gas leaks. Moreover, a minimal amount of force is required to break its seal, which may accidentally be broken, so the gas cartridge must be handled with great care. This solution additionally requires use of a specially designed gas cartridge and is thus not suitable for use with standard gas cartridges.

Another pressurized gas cartridge is disclosed in U.S. Pat. No. 7,156,257, issued Jan. 2, 2007. The gas cartridge features a clamped membrane which, instead of being flat, is concave and has a bump toward the inside of the cartridge. The shape of this membrane allows the use of a thinner membrane, compared to a conventional flat membrane design. Use of this thinner membrane to safely and effectively seal the pressurized gas cartridge should make the membrane easier to break. Additionally, this recessed membrane design does not suffer from any transportation or handling issues. However, there remains a problem of reducing the required force for puncturing a curved membrane. The design is also expected to involve increases in manufacturing complexity and in associated cost. Finally, this solution is not suitable for use with standard gas cartridges.

Introducing a new type of gas cartridge would, for some applications, require approval by regulating institutional bodies related to the transportation industry, to healthcare services, to the protection of the environment, and the like. Obtaining regulatory approval for a new type of gas cartridge could lead to development delays and cost increase.

Therefore, there is a need for an improved technique for puncturing pressurized gas cartridges.

SUMMARY

According to the present disclosure, there is provided a mechanism for puncturing a gas cartridge. The mechanism comprises a lever having a pivot. A short lever arm and a long lever arm both extend from the pivot. The mechanism also comprises a ramp for pushing laterally a tip of the long lever arm under application of an input force on the ramp. The lever is configured to rotate about the pivot under lateral movement of the tip of the long lever arm, causing a tip of the short lever arm to apply a puncturing force between the gas cartridge and a puncturing member.

The present disclosure also relates to a gas injection device incorporating a mechanism for puncturing a gas cartridge.

The present disclosure further relates to a needleless syringe incorporating a mechanism for puncturing a gas cartridge.

The foregoing and other features will become more apparent upon reading of the following non-restrictive description of illustrative embodiments thereof, given by way of example only with reference to the accompanying drawings.

BRIEF DESCRIPTION OF THE DRAWINGS

Embodiments will be described in the following disclosure by way of example only with reference to the accompanying drawings, in which.

DETAILED DESCRIPTION

Various aspects of the present disclosure generally address one or more of the problems of puncturing pressurized gas cartridges, including currently available or future gas cartridges. More specifically, the present disclosure describes a mechanism using leverage for puncturing a membrane, for example a clamped membrane of a pressurized gas cartridge.

The following terminology is used throughout the present disclosure:

Mechanical advantage: a measure of force amplification.

Gas cartridge: a sealed, generally tubular container filled with gas at a pressure exceeding atmospheric pressure.

Puncturing: piercing with a pointed instrument.

Puncturing member: a pointed instrument such as a punch.

Lever: an elongated, rigid element for transmitting a force.

Fixed position: position that does not change in relation to the whole of a mechanism.

Main body: a part of a device for holding or receiving other parts.

Exhaust duct: a conduit or aperture for expelling gas from a cartridge.

Actuator: a mechanical part for exerting a movement on a device, for example by hand.

Pivot: an element about which another element may rotate.

Short-lever-arm tip: a free end of a relatively short lever arm.

Long-lever-arm tip: a free end of a relatively long lever arm.

Seat: a mechanical part in which one or more parts may rest.

Ramp: a graded or sloped surface.

Input force: force applied on an actuator, for example manually by a user.

Puncturing force: force effective in puncturing a membrane.

Multiplication factor: a factor of force amplification.

Friction losses: wasted energy within a mechanism, clue to friction or to viscous resistance to movement between components of the mechanism.

Opposed levers: levers that are facing each other.

Various embodiments of a mechanism for puncturing a gas cartridge, as disclosed herein, may be envisioned. One such embodiment comprises a puncturing mechanism that amplifies an input force applied by the user into a puncturing force for piercing a membrane, for example a clamped membrane of a pressurized gas membrane, for example a disposable pressurized gas cartridge to thereby release pressurized gas contained in the cartridge. More specifically, the present disclosure provides an arrangement of levers and ramps capable of meeting with these objectives. By combining two force multipliers in a certain way, a mechanical advantage sufficient to release the gas from a pressurized gas cartridge is obtained. Schematically, a ramp set in motion by the user with a small force pushes on a tip of a long arm of a lever while, in turn, rotation of the lever about a pivot engages a tip of a short lever arm of the same lever to push on the cartridge bottom, or on the puncturing member, so that the membrane gets perforated by the puncturing member to release the gas. A force multiplication factor of the assembly, obtained from a geometry of the lever and of the ramp, provides an overall mechanical advantage sufficient to puncture the membrane of the pressurized gas cartridge.

In a non-limitative example, the puncturing mechanism may be implemented in a needleless syringe, wherein the mechanism can be operated by a physician or a nurse with a single hand. The puncturing mechanism may also be used for multiple other applications, including for example inflatable floatation devices, emergency cartridges for inflating flat tires, various types of chemical trigger devices, and the like.

Figure 1:
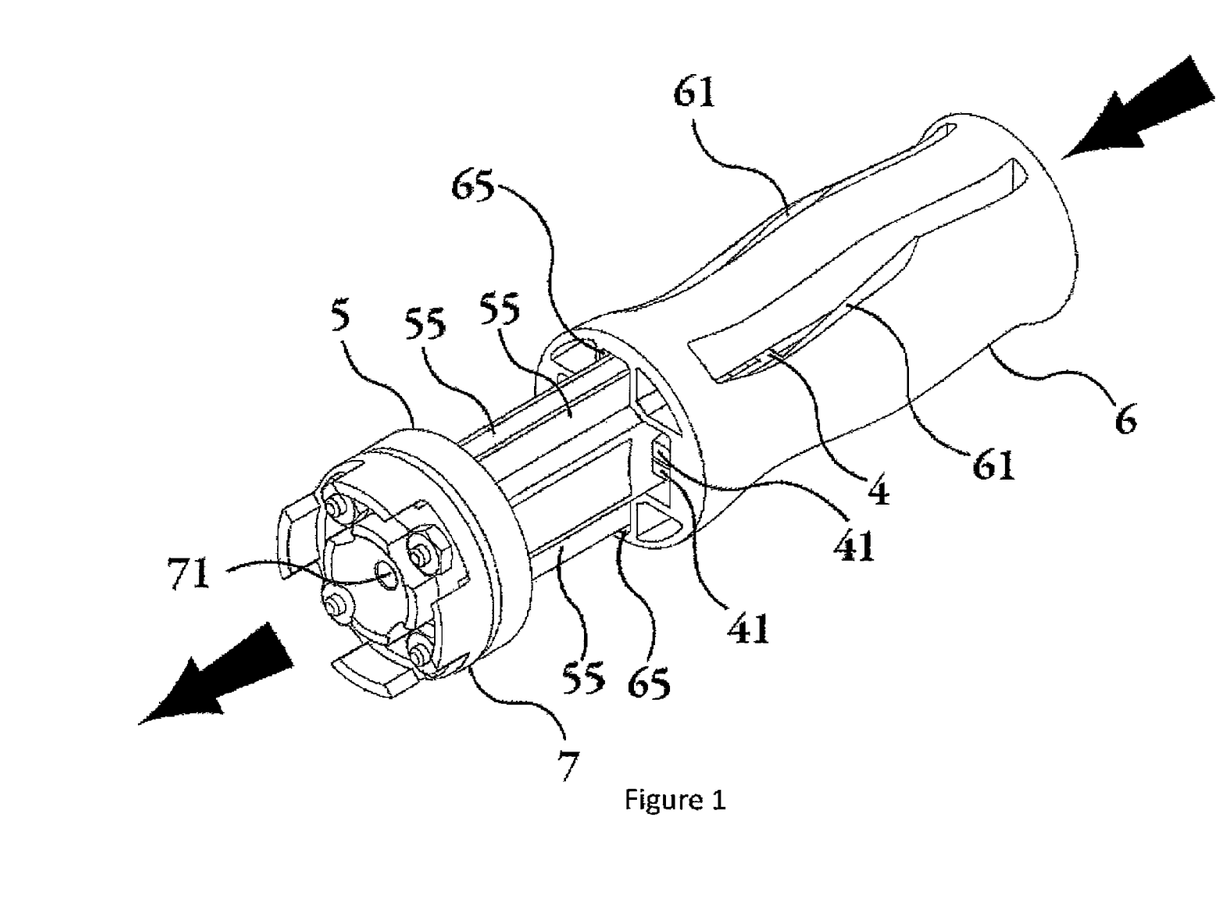
FIG. 1 is a perspective view of a gas injection device employing a mechanism for puncturing a gas cartridge, according to an embodiment.
Figure 2:
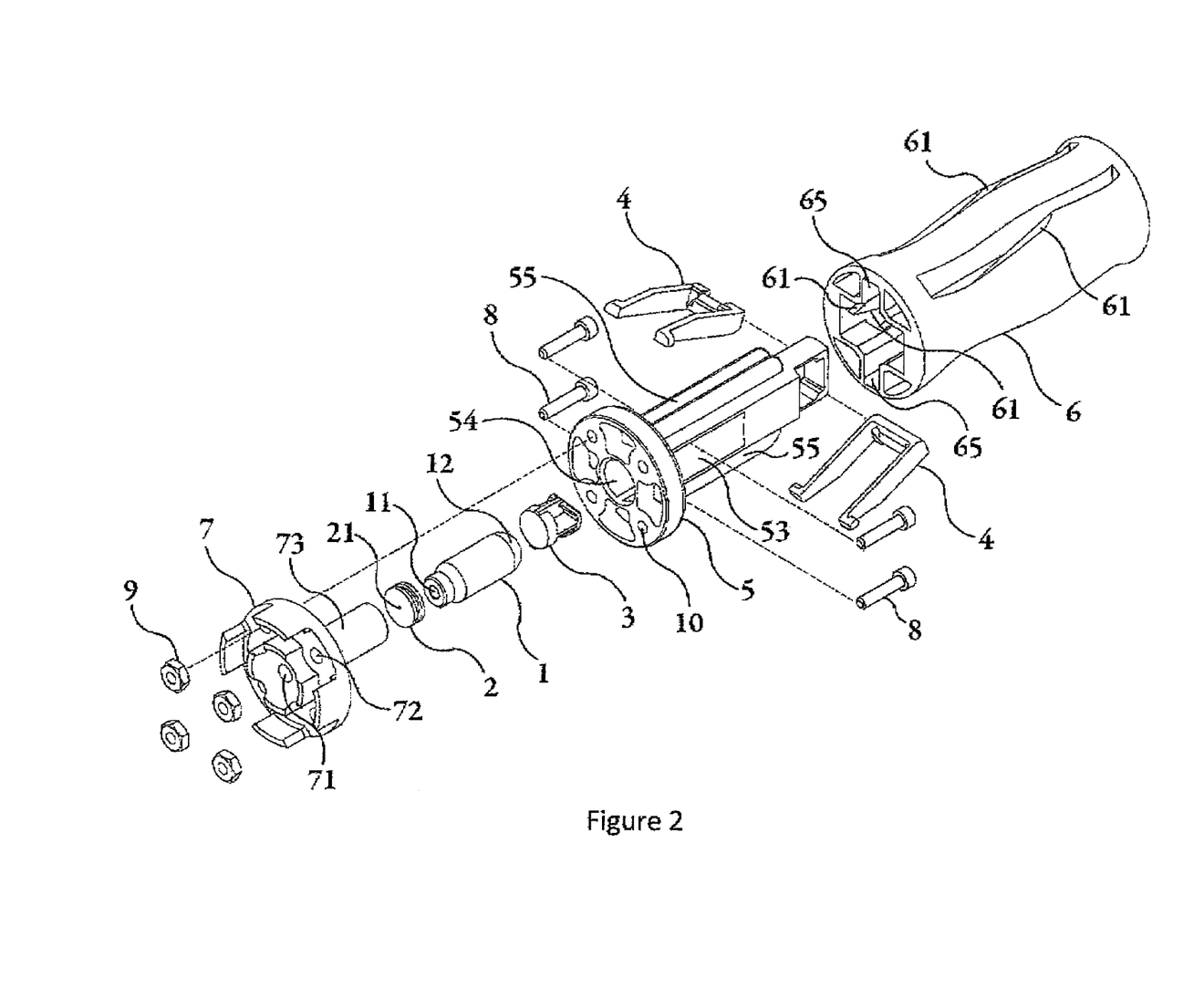
FIG. 2 is a perspective, exploded view of the device of FIG. 1.

Referring now to the drawings, FIG. 1 is a perspective view of a gas injection device employing a mechanism for puncturing a gas cartridge, according to an embodiment. FIG. 2 is a perspective, exploded view of the device of FIG. 1. The mechanism features a symmetric arrangement having two levers 4. In the shown embodiment, the mechanism pushes a pressurized gas cartridge 1 on a static puncturing member 2, for example a punch. A slightly different embodiment in which a gas cartridge is static and a puncturing member is moveable may also be implemented in a similar yet inverted configuration. The gas cartridge 1, the puncturing member 2 and the two levers 4 are received within a main body 5. Sliding a handle 8 over the main body 5 activates the mechanism. The handle 6 may act as an actuator of the mechanism for puncturing the gas cartridge. For this to happen, an exhaust 7 is kept still, for example by placing it on a still surface while the user pushes on the handle 6, sliding if toward the main body 5. In this particular arrangement, the user's action, identified by an arrow on the right hand side of FIG. 1, is in the same direction as a displacement of the gas cartridge 1. The sliding movement of the handle 8 translates into a movement having less amplitude, but a stronger puncturing force applied by the mechanism for pushing the gas cartridge 1 onto the static puncturing member 2. It may be observed that, according to the requirements of other applications, the displacement of the gas cartridge 1 may be in an opposite direction from that of the user's action. In the embodiment as shown, the four ramps 81 are symmetric and are integrated into the handle 8.

Figure 3:
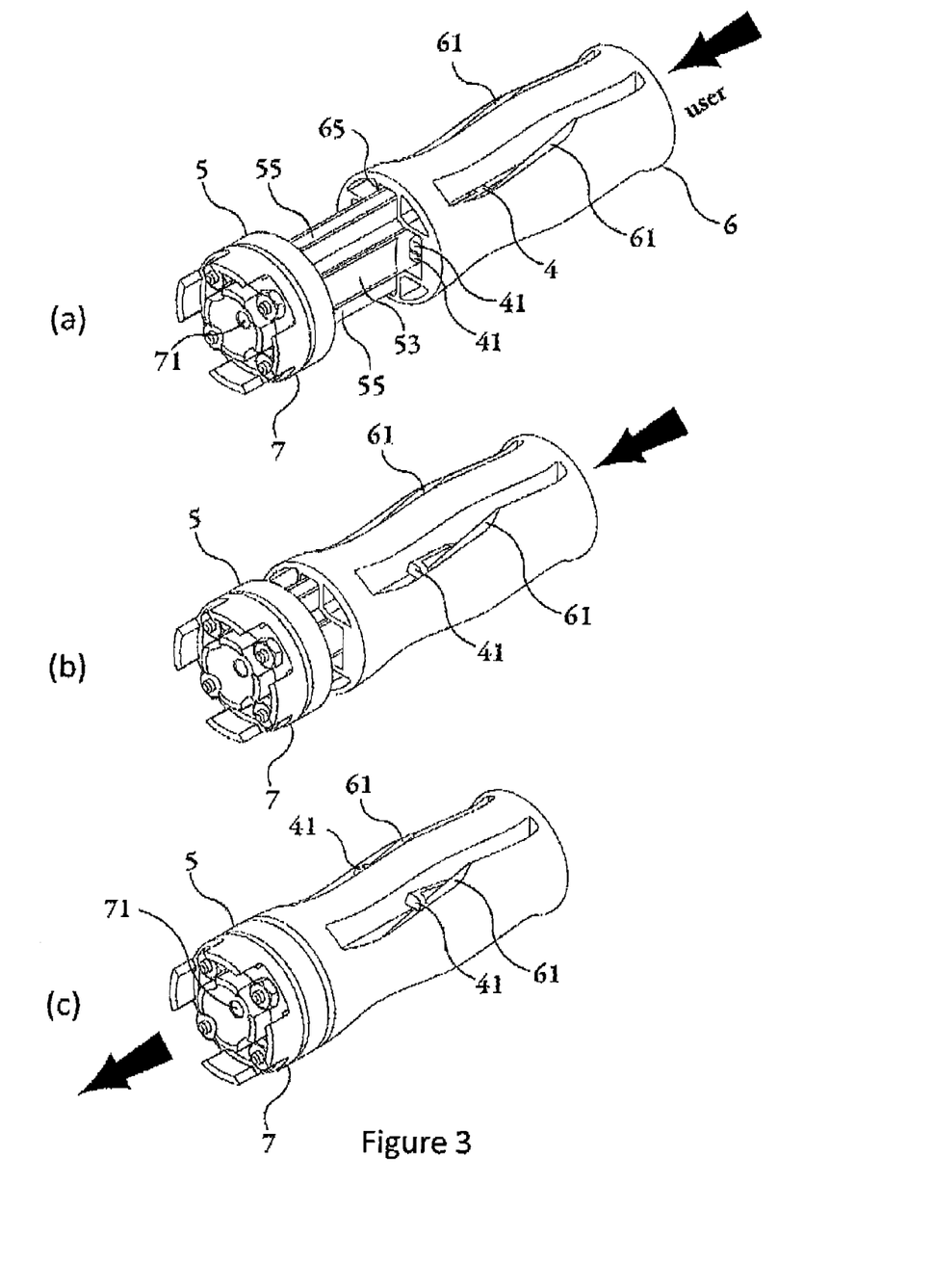
FIGS. 3a, 3b and 3c are perspective views of the device of FIG. 1 respectively before, during and at the conclusion of force application.
Figure 4:
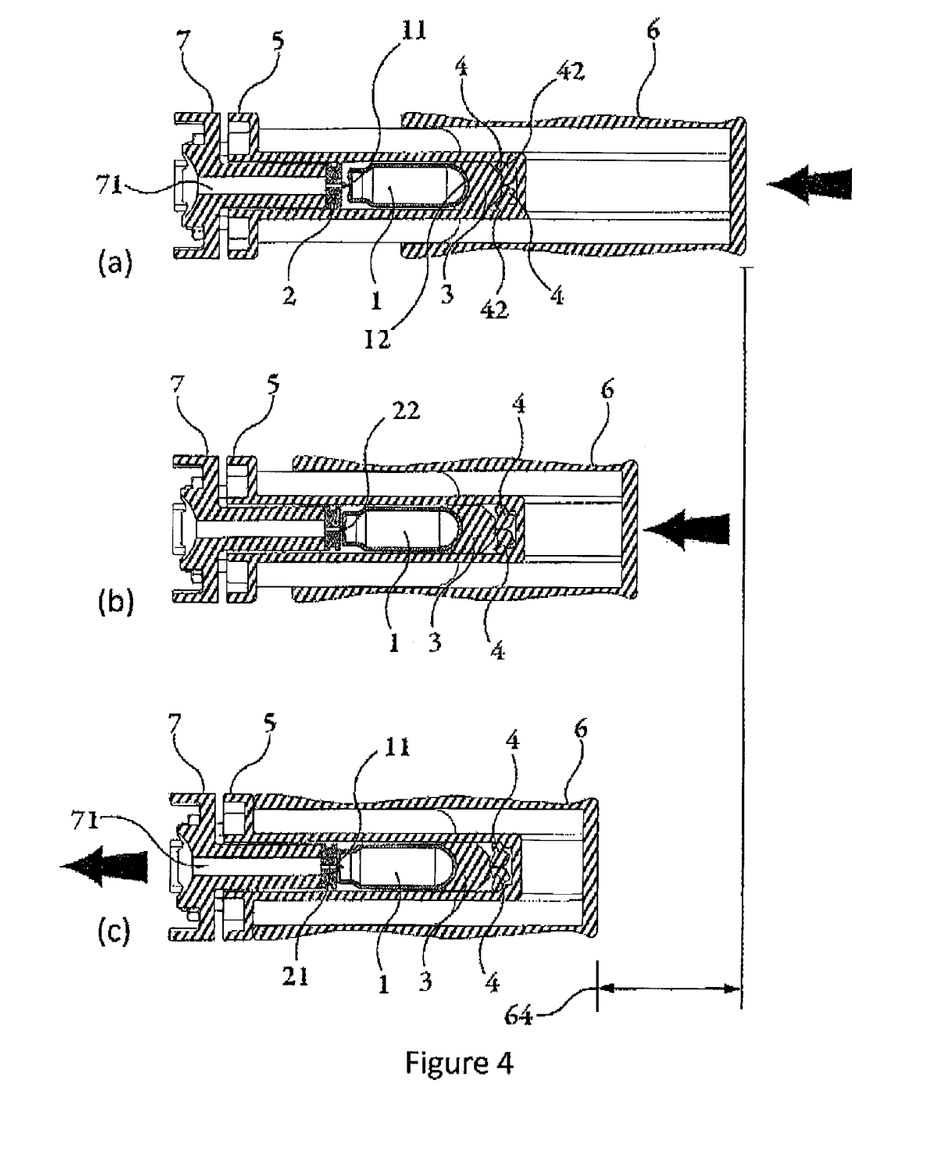
FIGS. 4a, 4b and 4c are side, cross sectional views of the device of FIG. 1 respectively before, during and at the conclusion of force application.
Figure 5:
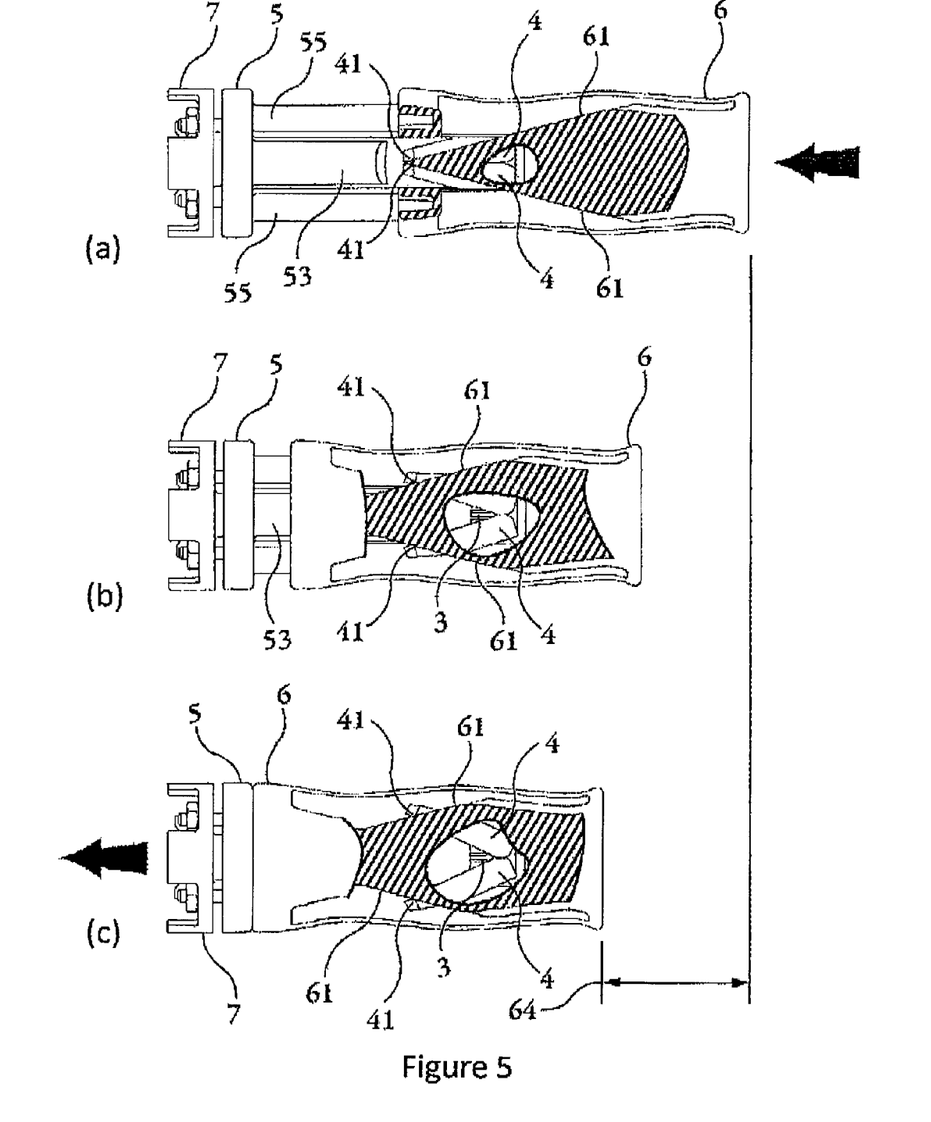
FIGS. 5a, 5b and 5c are side, partial cross sectional views of the device of FIG. 1 respectively before, during and at the conclusion of force application.
Figure 6:
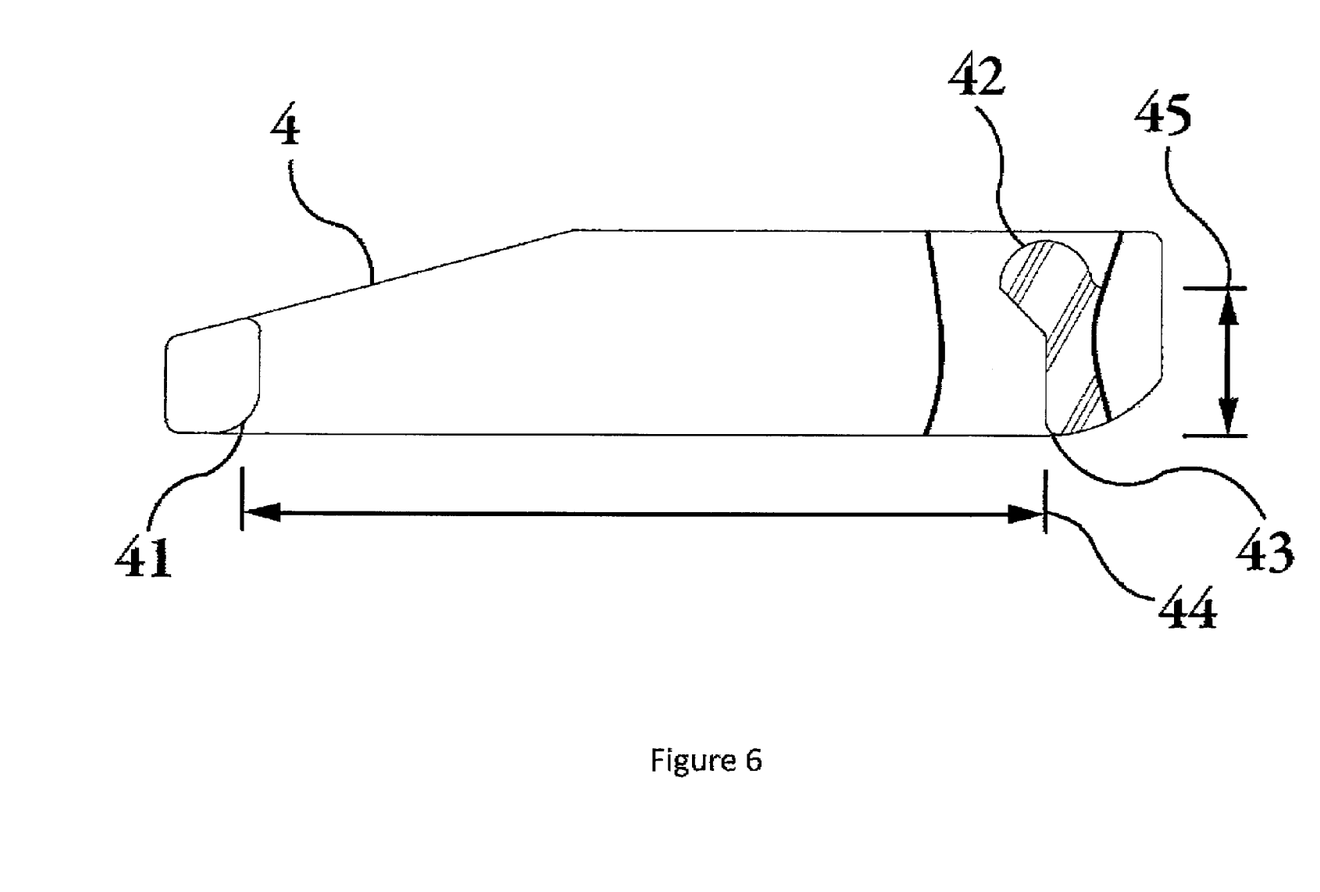
FIG. 6 is a detailed, partial cross sectional side view of a lever of the device of FIG. 1.

All parts of the device may be made of moldable plastic material and easy to assemble, thereby reducing the manufacturing cost per unit. The cartridge 1, including a membrane 11 that is intended to be punctured, may be made of stainless steel or similar material capable of withstanding high gas pressure. Puncturing the membrane 11 is made using the puncturing member 2 that may also be made at least in part of stainless steel or another suitable metal. Apart from these two pieces of metal, the entire device may be molded with plastic. Indeed, bolts 8 and nuts 9, which retain the exhaust 7 and the main body 5 together when the membrane 11 is pressed against the puncturing member 2, may easily be replaced by other removable or permanent metal-free fasteners made to accommodate an intended usage of the device, whether the device is a single use, disposable or reloadable device. As non-limiting examples, the bolts 8 and nuts 9 may be replaced by snap-fit arrangement, molded threads, glue, ultrasonic welding, and the like, FIGS. 3a, 3b and 3c are perspective views of the device of FIG. 1 respectively before, during and at the conclusion of force application. FIGS. 4a, 4b and 4c are side, cross sectional views of the device of FIG. 1 respectively before, during and at the conclusion of force application. FIGS. 5a, 5b and 5c are side, partial cross sectional views of the device of FIG. 1 respectively before, during and at the conclusion of force application. FIG. 6 is a detailed, partial cross sectional side view of a lever of the device of FIG. 1. Operation of the device will be best understood by considering FIGS. 3a-3c to 5a-5c and 6 in combination.

FIGS. 3a, 4a and 5a show the handle 6 mounted in a resting position by sliding on the main body 5. As the handle 6 is pushed by the user to slide further on the main body 5, toward the exhaust 7 (see arrow of users action on FIGS. 3a-3c to 5a-5c), tips 41 of long lever arms of the levers 4 slide on the ramps 61 of the handle 6 and are pushed laterally outwardly, more specifically spread apart making the levers 4 to revolve about cylindrical pivots 42. Thereby, tips 43 of short lever arms of the levers 4 are forced against the back of a piston 3, which in turn transmits the puncturing force on a bottom 12 of the cartridge 1, so that the membrane 11 is pressed against and punctured by the puncturing member 2. Each lever 4 as shown comprises two long-arm tips 41 forming a U-shape with the pivot 42 located between the two long-arm tips 41. The two levers 4 are symmetrically opposed, facing each other within the main body 6. Pushing the two levers 4 laterally, in opposite directions, results in spreading apart the two levers 4. In a simpler embodiment, the device may comprise use a single lever having a single long-lever-arm tip. A single ramp pushing the long-lever arm tip of this lever laterally still makes this lever revolve about a pivot, resulting in a short-ever-arm tip being forced against the back of the piston 3. While a single lever and a single ramp may be used, the embodiment as shown uses the two levers 4 and the four ramps 61 to balance induced lateral forces.

A function of the piston 3 is to accommodate for different pressurized gas cartridge lengths and shapes. In some embodiments, the piston 3 could be shortened or even omitted.

When the puncturing member 2 pierces the membrane 11, the membrane 11 may create a seal surrounding the puncturing member 2 thereby leaving a center hole 21 made by the puncturing member 2 as the sole exit for the released gas. Alternatively, for some applications, a tip 22 of the puncturing member 2 may be cut at an angle to prevent this sealing effect. Released gas finally flows out of the mechanism by an exhaust duct 71 built within the exhaust 7 and may then serve to supply an intended device or activate an intended application.

Figure 7:
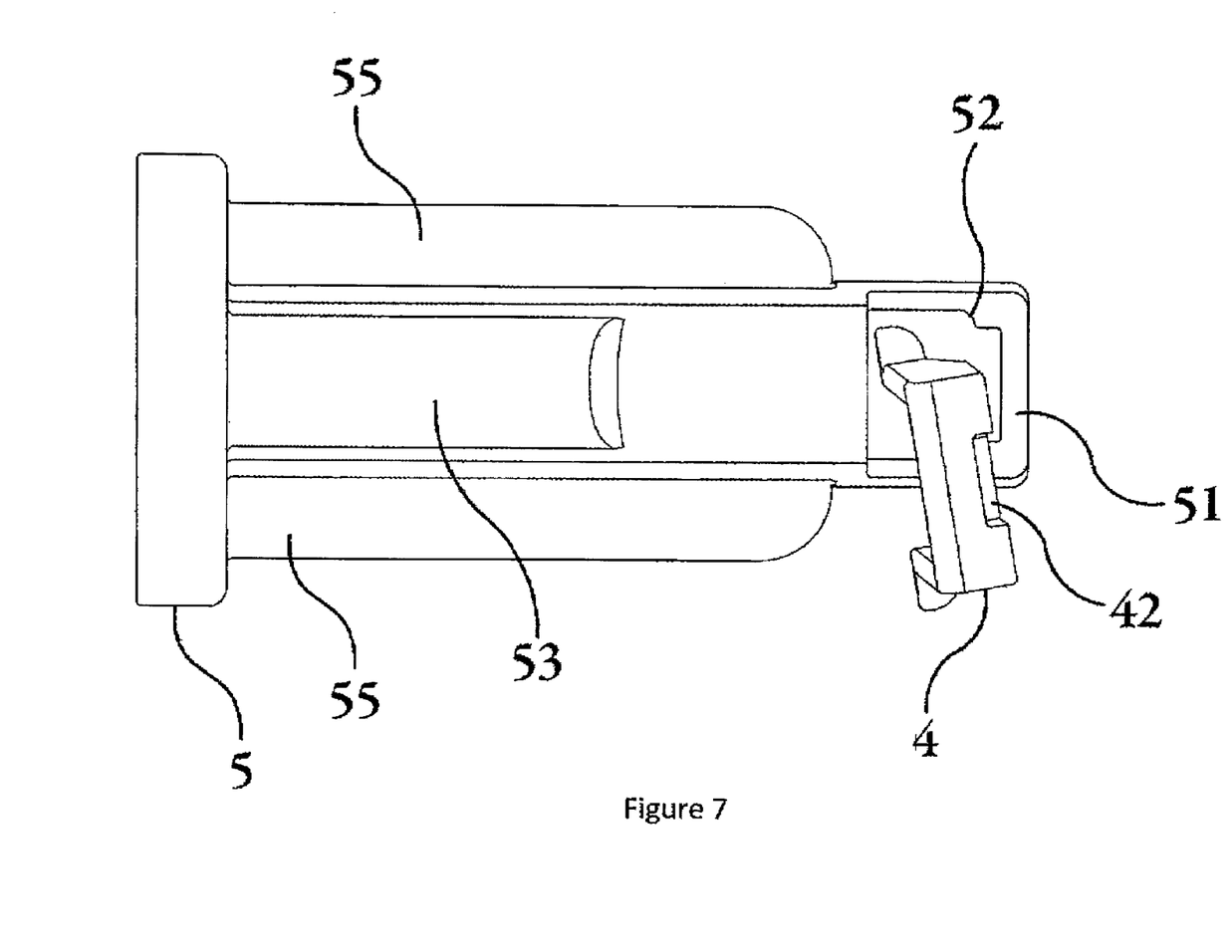
FIG. 7 is a side view showing details of insertion of one of the levers in the main body of the device of FIG. 1.
Figure 8:
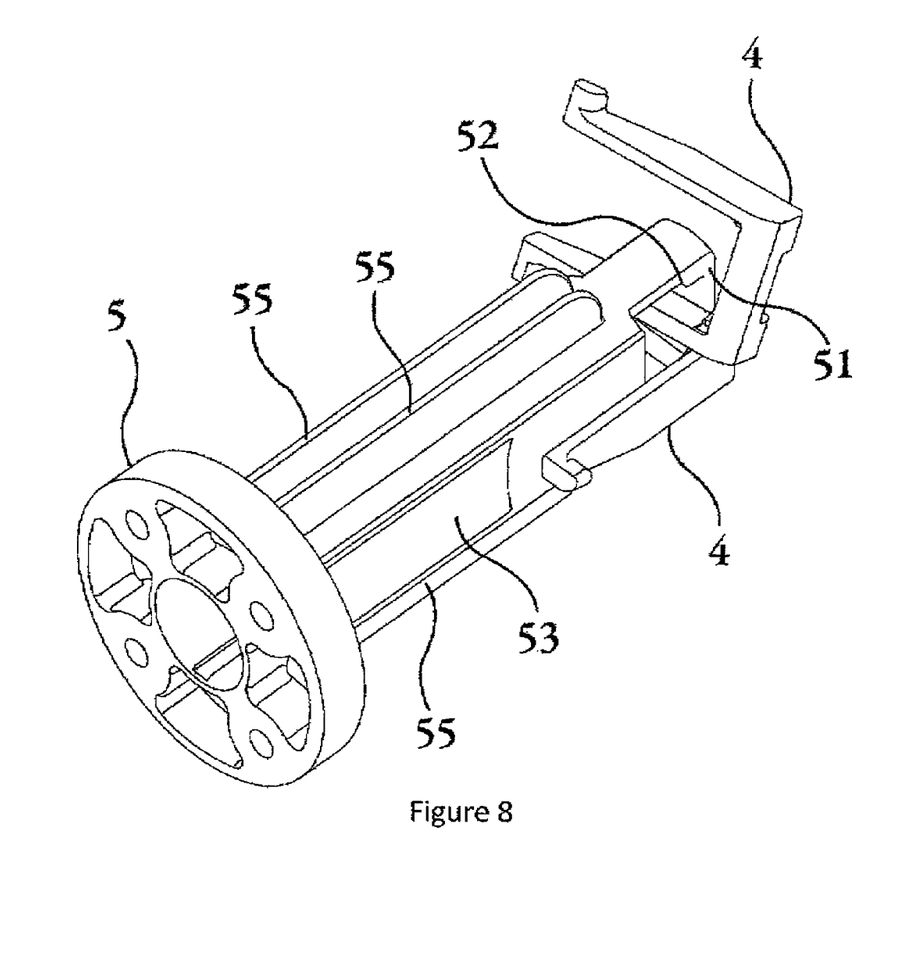
FIG. 8 is a perspective view showing additional details of insertion of the lever in the main body of the device of FIG. 1.
Figure 9:
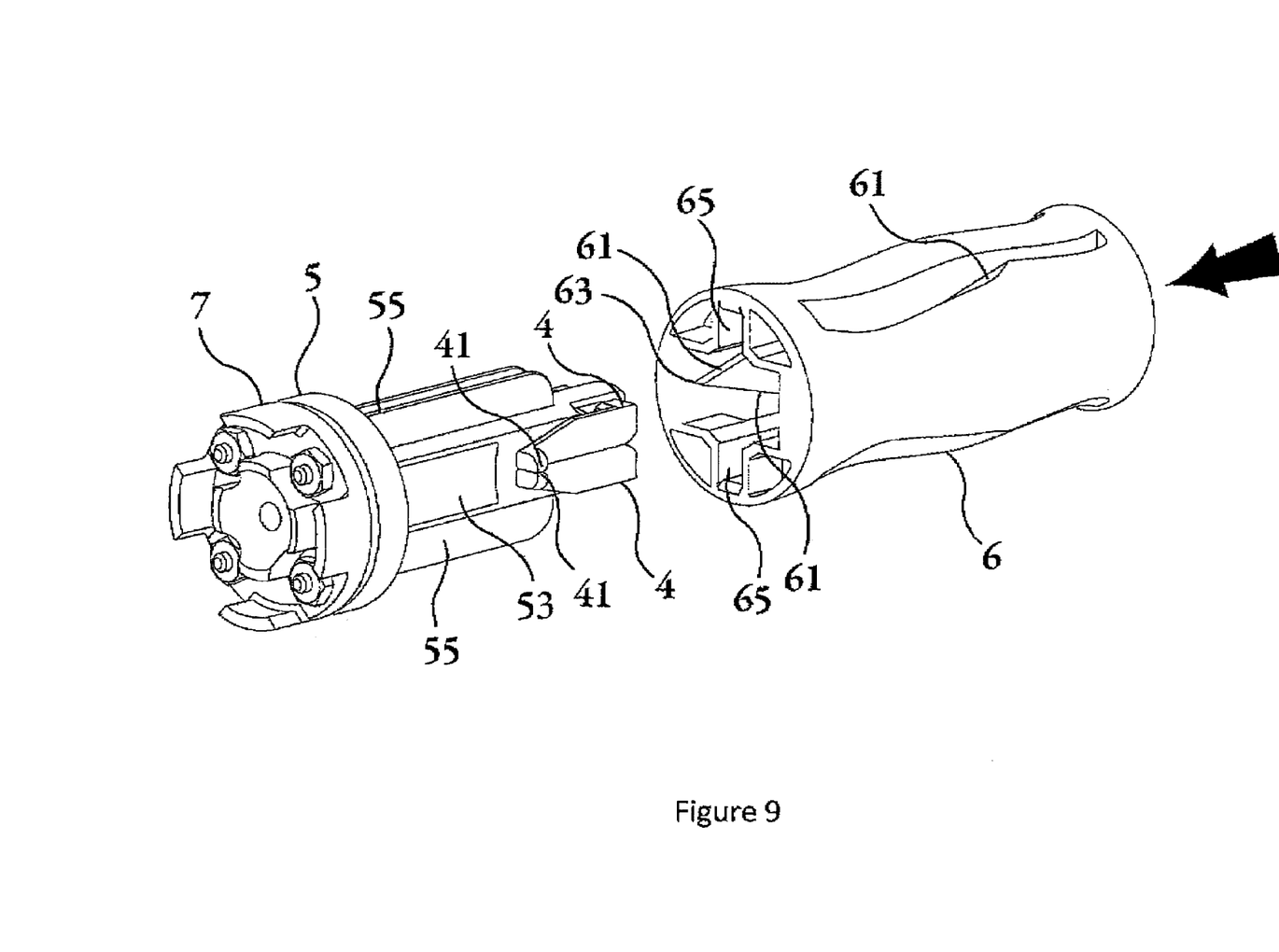
FIG. 9 shows a method of mounting an actuator on the main body of the device of FIG. 1.

FIG. 7 is a side view showing details of insertion of one of the levers in the main body of the device of FIG. 1. FIG. 8 is a perspective view showing additional details of insertion of the lever in the main body of the device of FIG. 1. FIG. 9 shows a method of mounting an actuator on the main body of the device of FIG. 1. The device of FIG. 1 may be assembled as follows. First, as shown on FIGS. 7 to 9, two U-shape levers 4 are inserted into a loop 51, molded in the main body 5, so that the cylindrical pivot 42 fits onto a seat 52. Referring again to FIG. 2, the piston 3, the cartridge 1, the puncturing member 2 and a stem 73 of the exhaust 7 are axially inserted, in this order, info a cylindrical chamber 53 of the main body 5 via a circular opening 54 at the front of the main body 5. The bolts 8 are then inserted into holes 10 of the main body 5 and into holes 72 of the exhaust 7, whereafter the nuts 9 are lightly screwed on the bolts 8 until there is no gap between the puncturing member 2 and the membrane 11. Leaving a gap would unnecessarily lengthen travel of the cartridge 1 and therefore would result in an overall longer system. Once the exhaust 7 and the levers 4 have been mounted to the main body 5, the handle 6 is slipped over the main body 5 by sliding inner longitudinal grooves 85 of the handle 6 over longitudinal fins 55 of the main body 5. The handle 6 is slid onto the main body 5 until the resting position is reached when points 63 formed by the ramps 81 get in contact with the long-arm tips 41 of the levers, between these tips 41. The device, as shown on FIG. 1, is now ready to be used. The user may now slide the handle 6 in the direction as shown on the Figures to thereby puncture the membrane 11 of the gas cartridge 1.

An embodiment of the mechanism shown on FIG. 1 delivers a force multiplication factor in which a force applied by the user's operation of the handle 8 is multiplied by a leveraging effect to provide a mechanical advantage to puncture the membrane 11 of the gas cartridge 1. A theoretical multiplication factor may be estimated based on a geometry of the mechanism within the device of FIG. 1 for example on lengths of the long and short lever arms of the levers 4. However, an actual mechanical advantage will differ due for example to friction losses within the device including friction of the long-arm tips 41 on the ramps 81, friction of the pivots 42 in the seat 52, friction of the piston 3 inside the main body 5, friction of the inner longitudinal grooves 65 of the handle 8 over the longitudinal fins 55 of the main body 5, and so on.

The geometry of the device of FIG. 1 provides a multiplication of a force applied on the handle 6 for puncturing the gas cartridge 1. In an embodiment shown on FIG. 4, the membrane 11 of the gas cartridge 1 requires a 1-mm displacement of a tip 22 of the puncturing member 2 to overcome its plasticity and release the gas. The tip 22 of the puncturing member 2 therefore has a 1-mm height. From this, a relative movement bringing the gas cartridge 1 and the puncturing member 2 closer by 1 mm is sufficient to puncture the gas cartridge 1. A ratio of a distance of movement of the handle 6, in the direction of displacement of the handle 6 towards the main body 5, over this 1-mm distance of relative movement between the gas cartridge 1 and the puncturing member is equal to the theoretical multiplication factor of the force. The geometry of device of FIG. 1 provides a theoretical force multiplication factor of 25, which means that, assuming no energy loss due to friction between moving parts, there is theoretically a 25-Newton acting force at the puncturing member-membrane interface for each Newton of force applied by the user.

This total theoretical force multiplication factor of 25 is given by the product of force gains from each force multiplier used within the device of FIG. 1. The force multipliers are the levers 4 and the ramps 61.

Referring back to FIG. 6, the force gain of the levers is given by the ratio of a length 44 of a lever arm between the pivots 42 and the long-lever-arm tips 41 over a length 45 between the pivots 42 and the short-lever-arm tips 43. The force gain of the levers 4 is 6.25, this value being obtained with the length 44 of the long lever arm (22.5 mm in this example) divided the length 45 of the short lever arm (3.6 mm in this example). Of course, these values relate to a specific realization of the device of FIG. 6. Other embodiments may use different sizes or different relative lengths of the long and short lever arms.

Figure 10:
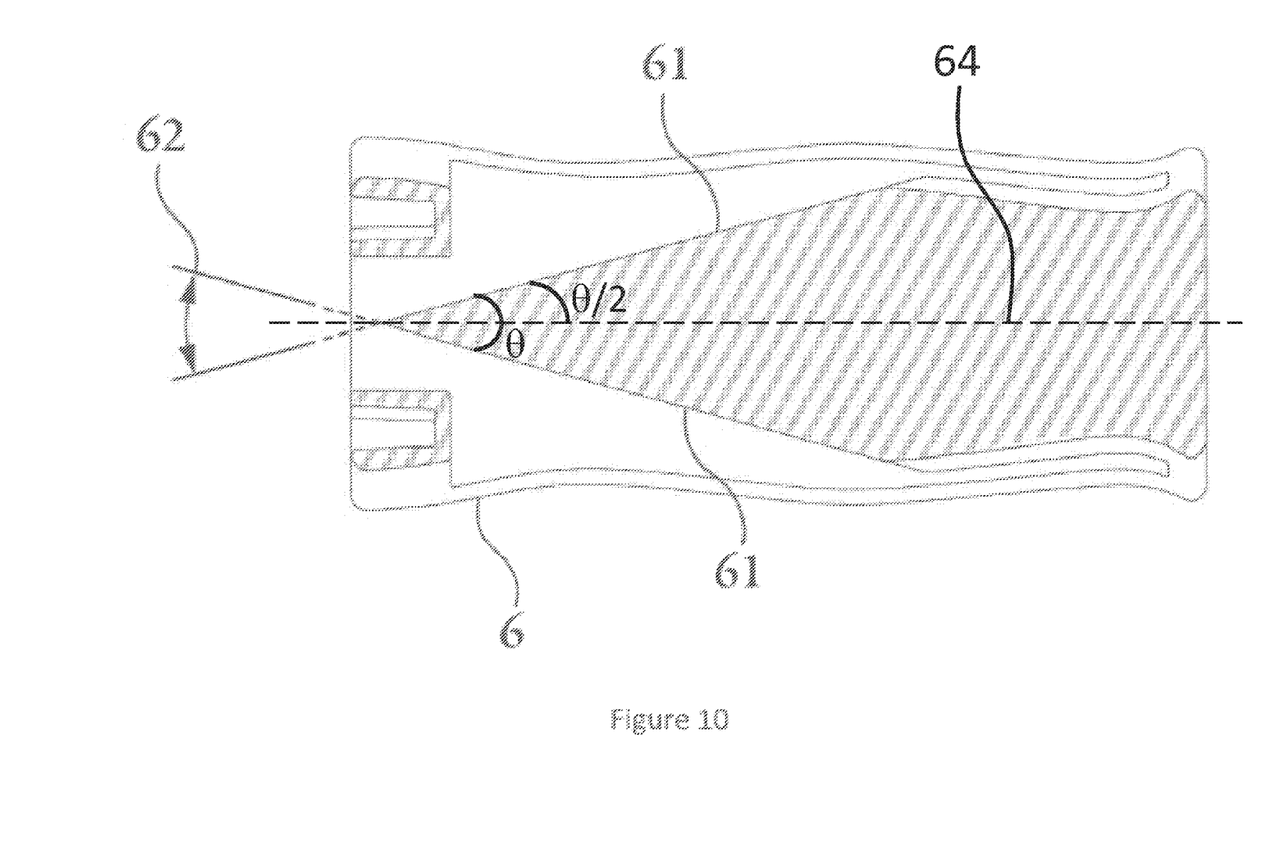
FIG. 10 shows details of the ramps within the actuator of the device of FIG. 1.

As disclosed hereinabove, the ramps 61 form a second force multiplier. FIG. 10 shows details of the ramps within the actuator of the device of FIG. 1. On FIG. 10, an angle 62 (θ) represents a contribution of slopes from two ramps 61. A force gain of the ramps 61 is given by $$G2 = \frac{1}{\sin(\theta/2)}.$$

In an embodiment, the force multiplication factor of the ramps 61 is 4, this value being obtained with an angle 62 (θ)

of 29 degrees, or 14.5 degrees between each ramp 81 and a longitudinal axis 64 of the handle 6.

Friction within the device of FIG. 1 may depend on many factors, including for example materials used for making the various moving parts, finish of mating surfaces, ambient conditions, and the like. In order to determine an actual multiplication factor of the device, a prototype was built to puncture a 1 ml pressurized gas cartridge filled with $N_2$ at 20 MPa, which is about 200 times the atmospheric pressure. The gas cartridge selected for testing the prototype required a puncturing force of about 187 Newton (N) applied with a travel of the puncturing member of about 1 mm. Other design constraints of the prototype were that the entire device should fit in a hollow cylinder of 30 mm inside diameter, this size being selected to fit in an average user hand, and that the user input force should be less than about 13 N, a force that most persons would qualify as easy to apply. An effective, as opposed to theoretical, force multiplication factor may be computed as a ratio of the puncture force over the user input force, which in the case of the gas cartridge selected for testing the prototype amounted to 187 N divided by 13 N, yielding an effective force multiplication factor of 14.4. A difference between the theoretical force multiplication factor of 25 of the device of FIG. 8 and the effective force multiplication factor of 14.4 represents a maximum amount of friction losses within the device.

Though the ramps 61 illustrated in the preceding Figures are linear, nonlinear or curved ramps may be used in a variant. The force multiplication factor conferred to the mechanism by varying curved ramp angles θ may be modulated as a function of the displacement of the handle 6 towards the main body 5. The tips 41 of the long lever arms of the levers 4 sliding on such curved ramps may then be pushed laterally outwardly in a nonlinear fashion. For example, a larger force multiplication factor may initially help in overcoming an initial static friction within the mechanism.

A moldable prototype was built, with a geometry providing a theoretical multiplication force factor of 25, using the lever arm lengths and ramps angles as defined in the previous paragraphs. The prototype was crafted using stereolithography—an additive rapid prototyping technology—using a resin mimicking polycarbonate in terms of mechanical properties. With this configuration, a rectilinear handle motion 84 range of the user input was limited to a 25 mm, and a force of 12.5 N, slightly less than the design constraint of 13 N, was measured. The theoretical force multiplication factor of 25 thus provided an effective force multiplication factor of 15, calculated as a ratio between the puncturing force of 187 N over the measured force of 12.5 N. The effective force multiplication factor was somewhat superior to the computed minimal force multiplication factor of 14.4.

Due to the fabrication process of the prototype, which involved deposition of material by layers, and due to a choice of materials, silicone grease was added on the ramps to prevent the tips of the levers from sticking at the beginning of the actuation. For applications in which the use of a lubricant would be less practical, friction-critical parts of the mechanism may alternatively be molded using self-lubricating plastic, for example ultra-high-molecular-weight polyethylene (UHMWPE). The impact of friction losses on the effective force multiplication factor may be further reduced by conferring a mirror-like finish to moving parts at their friction points.

Figure 11:
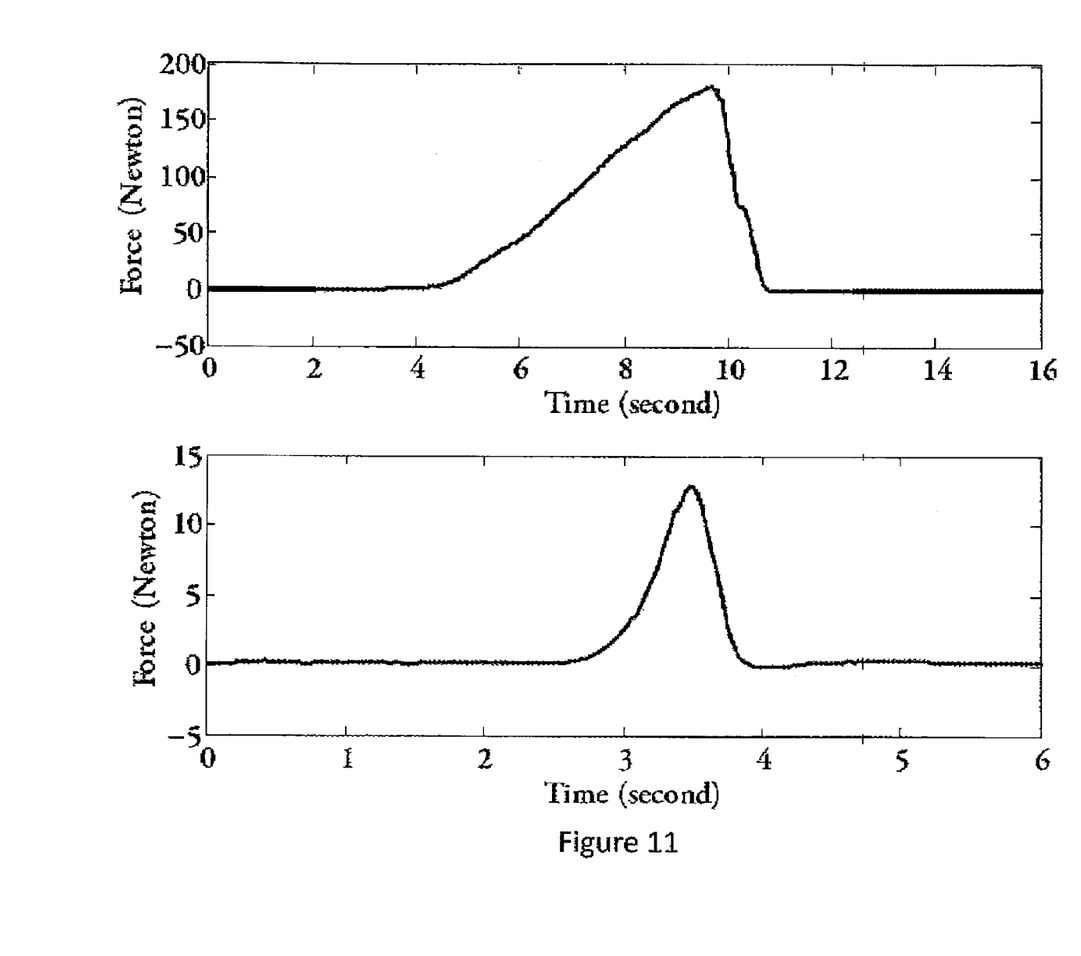
FIG. 11 shows graphs of a puncturing force (top) and of an input force (bottom).

FIG. 11 shows graphs of a puncturing force (top) and of an input force (bottom). As shown at the top of FIG. 11, puncturing the gas cartridge selected for testing the prototype using a punch and applying a direct force requires a minimal force of 187 N. Using the same punch integrated in the prototype allows puncturing an identical gas cartridge using a mere 13 N of input force applied by the user on the handle 8.

Those of ordinary skill in the art will realize that the description of the mechanism for puncturing gas cartridges are illustrative only and are not intended to be in any way limiting. Other embodiments will readily suggest themselves to such persons with ordinary skill in the art having the benefit of the present disclosure. Furthermore, the disclosed mechanism may be customized to offer valuable solutions to existing needs and problems of puncturing gas cartridges.

Those of ordinary skill in the art will also appreciate that numerous types of devices may embody aspects of mechanism for puncturing gas cartridges.

In the interest of clarity, not all of the routine features of the implementations of the mechanism for puncturing gas cartridges are shown and described. It will, of course, be appreciated that in the development of any such actual implementation of the mechanism, numerous implementation-specific decisions may need to be made in order to achieve the developers specific goals, such as compliance with application-, system-, and business-related constraints, and that these specific goals will vary from one implementation to another and from one developer to another. Moreover, it will be appreciated that a development effort might be complex and time-consuming, but would nevertheless be a routine undertaking of engineering for those of ordinary skill in the field of gas delivery systems having the benefit of the present disclosure.

Although the present disclosure has been described hereinabove by way of non-restrictive, illustrative embodiments thereof, these embodiments may be modified at will within the scope of the appended claims without departing from the spirit and nature of the present disclosure.

What is claimed is:

1. A mechanism for puncturing a gas cartridge, comprising:
    a lever comprising a pivot, a short lever arm and a long lever arm, both lever arms extending from the pivot; and
    a ramp for pushing laterally a tip of the long lever arm under application of an input force on the ramp;
    wherein:
        the lever is configured to rotate about the pivot under lateral movement of the tip of the long lever arm, causing a tip of the short lever arm to apply a puncturing force between the gas cartridge and a puncturing member;
        a ratio of a length of the long lever arm divided by a length of the short lever arm forms a first gain of the input force applied on the lever; and
        a second gain (G2) of the input force applied on the lever is according to:

$$G2 = \frac{1}{\sin(\theta/2)};$$

wherein θ/2 is an angle between the ramp and a longitudinal axis of the mechanism.

2. The mechanism of claim 1, comprising a fixed position of the gas cartridge, the tip of the short lever arm being capable of pushing the puncturing member against the gas cartridge.

3. The mechanism of claim 1, comprising a fixed position of the puncturing member, the tip of the short lever arm being capable of pushing the gas cartridge against the puncturing member.

4. The mechanism of claim 3, comprising a piston placed between the tip of the short lever arm and the gas cartridge for transmitting the puncturing force from the lever to the gas cartridge.

5. The mechanism of claim 1, comprising:
a main body for receiving the gas cartridge, the puncturing member and the lever.

6. The mechanism of claim 5, comprising:
an exhaust duct attached to the main body for releasing gas expelled from the gas cartridge.

7. The mechanism of claim 5, comprising:
an actuator for mounting on the main body, the actuator being capable of applying the input force on the ramp by sliding on the main body.

8. The mechanism of claim 5, wherein:
the lever comprises first and second symmetrically opposed long lever arms, the pivot being located between the first and second long lever arms, wherein the two long lever arms, the pivot and the short lever arm form a U-shaped lever.

9. The mechanism of claim 1, wherein:
the main body comprises a seat for receiving the pivot; and the tip of the short lever arm protrudes from the seat.

10. The mechanism of claim 1, wherein:
the puncturing force is proportional to values of the input force, of the first gain and of the second gain, minus friction losses within the mechanism.

11. The mechanism of claim 1, comprising:
a main body for receiving the gas cartridge, the puncturing member and the lever;
an actuator for slidably mounting to a resting position on the main body, the actuator being capable of sliding further on the main body for applying the input force on the ramp.

12. A gas injection device comprising the mechanism as claimed in claim 1.

13. A needleless syringe comprising the mechanism as claimed in claim 1.

14. A mechanism for puncturing a gas cartridge, comprising:
a pair of opposed levers, each lever comprising a pivot, a short lever arm and a long lever arm, both lever arms extending from the pivot, and
a pair of ramps for pushing laterally tips of long lever arms of each opposed levers under application of an input force on the ramps, thereby spreading apart the pair of opposed levers;
wherein each lever is configured to rotate about its pivot under lateral movement of the tip of its long lever arm, causing a tip of its short lever arm to apply a puncturing force between the gas cartridge and a puncturing member.

15. The mechanism of claim 14, comprising:
a main body for receiving the gas cartridge, the puncturing member and the pair of opposed levers; and
an actuator for mounting on the main body, the actuator being capable of applying the input force on the ramps by sliding on the main body.

16. The mechanism of claim 15, wherein:
the pair of opposed levers comprises two U-shaped opposed levers, each U-shaped opposed lever comprising first and second opposite long lever arms and a short lever arm, a pivot of each U-shaped opposed lever being located between the first and second long arms of each U-shaped opposed lever;
the main body comprises a seat for receiving the pivots;
a tip of each short lever arm protrudes from the seat;
the ramps are configured for spreading apart tips of the first and second long lever arms of one of the U-shaped opposed levers from tips of the first and second long lever arms of the other one of the U-shaped opposed levers upon sliding of the actuator on the body; and
the U-shaped opposed levers are configured to rotate about their pivots when the tips of their long lever arms are spread apart by the ramps, causing the tips of the short lever arms to apply the puncturing force between the gas cartridge and the punch.

17. A gas injection device comprising the mechanism as claimed in claim 14.

18. A needleless syringe comprising the mechanism as claimed in claim 14.

* * * * *